United States Patent
Bihler et al.

(10) Patent No.: US 11,456,277 B2
(45) Date of Patent: Sep. 27, 2022

(54) THERMOCOMPRESSION BONDING OF ELECTRONIC COMPONENTS

(71) Applicant: DYCONEX AG, Bassersdorf (CH)

(72) Inventors: Eckardt Bihler, Uitikon (CH); Marc Hauer, Uster (CH)

(73) Assignee: DYCONEX AG, Bassersdorf (CH)

( * ) Notice: Subject to any disclaimer, the term of this patent is extended or adjusted under 35 U.S.C. 154(b) by 0 days.

(21) Appl. No.: 17/034,723

(22) Filed: Sep. 28, 2020

(65) Prior Publication Data

US 2021/0098416 A1    Apr. 1, 2021

(30) Foreign Application Priority Data

Sep. 27, 2019 (EP) .................... 19200201

(51) Int. Cl.
*H01L 21/56*    (2006.01)
*H01L 23/31*    (2006.01)
(Continued)

(52) U.S. Cl.
CPC .......... *H01L 24/81* (2013.01); *H01L 21/4853* (2013.01); *H01L 21/563* (2013.01);
(Continued)

(58) Field of Classification Search
CPC ........... H01L 24/81; H01L 2224/81203; H01L 21/563
See application file for complete search history.

(56) References Cited

U.S. PATENT DOCUMENTS 6,204,163 B1 * 3/2001 Panchou ................ H01L 24/81
257/E21.511

9,293,438 B2    3/2016 Rendek, Jr. et al.
(Continued)

FOREIGN PATENT DOCUMENTS

EP    3413343 A2    12/2018

OTHER PUBLICATIONS

Xu K. et al: "A General Purpose Adhesive for Microelectronic Devices", International Journal of Microcircuits and Electronic Packaging, International Microelectronics & Packaging Society, US, vol. 23, No. 1, Jan. 1, 2000 (Jan. 1, 2000), pp. 78-84, XP000932571, ISSN: 1063-1674.

*Primary Examiner* — Dale E Page
*Assistant Examiner* — Wilner Jean Baptiste
(74) *Attorney, Agent, or Firm* — Laurence A. Greenberg; Werner H. Stemer; Ralph E. Locher

(57) ABSTRACT

A method for producing an electronic module includes providing a first substrate including at least one first electrical contacting surface, an electronic component including at least one second electrical contacting surface, and a first material layer made of a thermoplastic material including at least one recess extending through the material layer. The first substrate, the electronic component and the first material layer are arranged with the first material layer disposed between the first substrate and the electronic component, and the at least one first electrical contacting surface, the at least one second electrical contacting surface and the at least one recess aligned relative to one another. The first substrate, the electronic component and the material layer are thermocompression bonded. A joint formed between the at least one first electrical contacting surface and the at least one second electrical contacting surface is surrounded or enclosed by the first material layer.

19 Claims, 6 Drawing Sheets

(51) Int. Cl.
*H01L 23/00* (2006.01)
*H01L 21/48* (2006.01)

(52) U.S. Cl.
CPC .......... *H01L 23/3157* (2013.01); *H01L 24/13* (2013.01); *H01L 24/16* (2013.01); *H01L 2224/12105* (2013.01); *H01L 2224/13082* (2013.01); *H01L 2224/13144* (2013.01); *H01L 2224/13147* (2013.01); *H01L 2224/16157* (2013.01); *H01L 2224/81192* (2013.01); *H01L 2224/81203* (2013.01); *H01L 2924/1433* (2013.01); *H01L 2924/18161* (2013.01)

(56) References Cited

U.S. PATENT DOCUMENTS

| | | |
|---|---|---|
| 2011/0060206 A1 | 3/2011 | Schaaf et al. |
| 2015/0009644 A1* | 1/2015 | Rendek, Jr. .............. H05K 1/09 361/767 |
| 2015/0157862 A1 | 6/2015 | Greenberg et al. |
| 2017/0232250 A1 | 8/2017 | Kim et al. |
| 2018/0359874 A1 | 12/2018 | Hauer et al. |

* cited by examiner

THERMOCOMPRESSION BONDING OF ELECTRONIC COMPONENTS

CROSS-REFERENCE TO RELATED APPLICATION

This application claims the priority, under 35 U.S.C. § 119, of European Patent Application EP 19 200 201, filed Sep. 27, 2019; the prior application is herewith incorporated by reference in its entirety.

BACKGROUND OF THE INVENTION

Field of the Invention

The present invention relates to a thermocompression bonding method for joining electronic components.

Thermocompression bonding (TCB, also known as thermocompression welding) is a process known in electronics. The process is usually employed for connecting silicon chips including flip chip bumps (contacting bumps) to substrates (printed circuit boards).

The bumps, on the chip side, are pushed into contact surfaces (pads) of a substrate (printed circuit board) that are disposed in a mirror-inverted manner, and are welded together using heat and pressure. When the bumps and the pads are made of pure gold and are very clean during joining, the formation of an intermetallic phase at the interface between the bump and the pad can already be detected at pressures of a few bar and temperatures of 260° C. The connection is stable against shearing.

Metal-on-metal thermocompression bonding, however, is not widely used yet, compared to the soldering of flip chips using solder bumps, or the connection by way of anisotropic adhesives.

After the chip and the substrate have been joined, an underfill made of epoxy is usually introduced into the space between the chip and the substrate and cured.

The weak point of known joining techniques for microelectronics when used in implants and catheters is the electrical integrity of the packages against the ingress of liquids. The insulating properties of the materials used, in particular, degenerate as a result of penetrating liquid. In particular, the epoxy resins typically used in electronics are very susceptible to moisture. The electronic components have to be protected either by a metal housing made of titanium (state of the art for implants) or by another suitable additional sheathing (state of the art for catheters).

Another disadvantage of the packages known thus far is the interfaces between the different materials (substrate to underfill, underfill to silicon chip). Diffusion and dendritic growth can occur along those interfaces, and cracks can arise.

BRIEF SUMMARY OF THE INVENTION

It is accordingly an object of the invention to provide a method for producing an electronic module, an electronic module and a medical device, which overcome the hereinafore-mentioned disadvantages of the heretofore-known methods, modules and devices of this general type and in which the method is simple and the electronic module is, in particular, better and more reliably protected against environmental conditions.

With the foregoing and other objects in view there is provided, in accordance with the invention, a method for producing an electronic module. The method comprises the following steps:

providing a first substrate including at least one first electrical contacting surface, an electronic component including at least one second electrical contacting surface, and a first material layer made of a thermoplastic material including at least one recess that extends through the material layer;

arranging the first substrate, the electronic component and the first material layer so that the first material layer is disposed between the first substrate and the electronic component, and the at least one first electrical contacting surface, the at least one second electrical contacting surface and the at least one recess are aligned with respect to one another; and thermocompression bonding or welding the first substrate, the electronic component and the material layer, so that a joint is formed between the at least one first electrical contacting surface and the at least one second electrical contacting surface, and the joint is surrounded or enclosed by the first material layer.

The term "thermocompression bonding" also known as thermocompression welding, is used in the context of the present description in the meaning understood by a person skilled in the art, and in particular refers to a joining method in which two elements to be joined are interconnected using pressure and heat.

In particular, thermocompression bonding is carried out using uniaxial pressure and heat.

Moreover, the first substrate, the first material layer and the electronic component are aligned with one another in such a way that the at least one recess of the first material layer is disposed exactly between the at least one first contacting surface and the at least one second contacting surface. This configuration ensures that the two contacting surfaces are connected to form a joint during thermocompression bonding, yet, the arising joint is enclosed or encapsulated by the first material layer at the same time.

The first substrate and/or the first material layer preferably include alignment marks, based on which the configuration or the alignment can be carried out.

According to one embodiment of the method according to the invention, it is provided that the substrate and/or the first material layer consist of or include a liquid crystal polymer. Among the plastic materials, inert thermoplastic materials have the lowest permeability to water and gases. In particular, the group of the liquid crystal polymers (LCP) stands out among the polymers having the lowest water or gas permeability. The tightness of microelectronic packages can be considerably enhanced through the use of LCP. This also allows the critical dimensions (distances with respect to the surrounding area, material thickness) to be reduced. At the same time, this may be integrated into existing methods, thereby representing a very cost-effective implementation. Since LCP is a thermoplastic material, the interfaces can melt during the thermal processes, and the interface effects are considerably reduced.

Within the meaning of the present invention, the term "liquid crystal polymer" is used in the meaning known to and commonly used by a person skilled in the art. A "liquid crystal polymer" refers in particular to an aromatic polymer, which has highly ordered or crystalline regions in the molten state or in solution. Non-limiting examples include aromatic polyamides such as aramid (Kevlar) and aromatic polyesters of hydroxybenzoic acid, such as a polycondensate of 4-hydroxybenzoic acid and 6-hydroxynaphthalene-2-carboxylic acid (Vectran).

In a preferred embodiment of the method according to the invention, it is provided that the first substrate is formed of a first thermoplastic polymer, preferably a first liquid crystal polymer, and the first material layer is formed of a second thermoplastic polymer, preferably a second liquid crystal polymer, wherein the first thermoplastic polymer has a higher glass transition temperature or melting temperature than the second thermoplastic material.

As a result of this embodiment, in particular the disadvantages of the state of the art with respect to the ingress of moisture into the package are avoided. Preferably, a liquid crystal polymer having the same chemical composition is selected for the first and second thermoplastic polymers, differing only by a suitable thermal pretreatment, which ensures that the melting points are at different temperatures. In this case, it can be achieved by the method according to the invention that the interfaces between the two thermoplastic liquid crystal polymers vanish completely.

Particularly, this is achieved when the method according to the invention is carried out at a temperature above the melting temperature of the second thermoplastic material (forming the first material layer), particularly the second liquid crystal polymer. In this case, the first material layer can melt completely and form an integral bond with the first substrate.

This integral bond at the interface between the first thermoplastic polymer (forming the first substrate), particularly the first liquid crystal polymer, and the second thermoplastic material (forming the first material layer), particularly the second liquid crystal polymer, may be further improved when the surface of the first substrate has a particularly high roughness or mechanically introduced structures, such as trenches or depressions into which the second thermoplastic polymer having the lower melting point, particularly the second liquid crystal polymer, can flow, creating a mechanical interconnection. Particularly by appropriately selecting the temperature profile, additional cross-linking (e.g. transesterification or transamidation) between the chains of the first thermoplastic polymer, particularly the first liquid crystal polymer, and the second thermoplastic polymer, particularly the second liquid crystal polymer, can take place, particularly provided the two thermoplastic polymers, particularly the two liquid crystal polymers, are organic polyesters or polyamides having the same composition.

Accordingly, it is provided in one embodiment of the method according to the invention that the substrate includes one or more recesses, in which particularly the second thermoplastic polymer, particularly the second liquid crystal polymer, of the first material layer can flow, or flows, during thermocompression bonding.

According to a further embodiment of the method according to the invention, it is provided that the at least one first contacting surface, or the at least one second contacting surface, includes a bump or solder ball, which in particular includes or consists of gold or gold-coated copper.

According to a further embodiment of the method according to the invention, it is provided that the at least one first contacting surface is constructed as a pad, wherein the pad is preferably made of copper and includes a bump that is preferably made of gold or gold-coated copper. In a further embodiment, the at least one second contacting surface is constructed as a pad, preferably made of gold, and optionally includes a bump, preferably made of gold (gold stud bump), made of gold-coated copper (copper pillar bump), tinned gold or tinned copper, or a solder ball (solder bump), preferably made of tin solder. (for example, Sn99, Ag0.3, Cu0.7 or another mixture of Sn, Ag and Cu, or, for example, Au80Sn20).

According to a further embodiment of the method according to the invention, it is provided that a second material layer made of a thermoplastic material is disposed on the electronic component and is joined to the electronic component before, during or after the thermocompression bonding. The second material layer is preferably joined or connected to the electronic component by thermocompression bonding, that is, using pressure and heat, or by adhesive bonding. In one embodiment, the second material layer includes a liquid crystal polymer or consists thereof.

According to a further embodiment of the method according to the invention, it is provided that the second material layer is constructed as a second substrate or cover film.

According to a further embodiment of the method according to the invention, it is provided that the first substrate is constructed as a circuit board, particularly a printed circuit board.

According to a further embodiment of the method according to the invention, it is provided that the electronic component is constructed as an integrated semiconductor component, in particular an application-specific integrated circuit (ASIC), a standard integrated circuit (standard IC) or a wafer-level chip scale package (WL-CSP).

According to another embodiment of the method according to the invention, it is provided that the configuration and thermocompression bonding are carried out using a device. The device preferably includes one or two holding units, which are constructed to hold the electronic component and/or the first substrate. The holding device is, or the holding devices are, preferably furthermore constructed to apply pressure to the electronic component and/or the first substrate. The holding device preferably includes a heating element, for example a heating plate, so as to provide the necessary heat for the thermocompression bonding process. The device preferably further includes a camera, by way of which the first substrate, the electronic components and the first material layer can be disposed or aligned, for example via alignment marks on the first substrate, the electronic component or the first material layer.

With the objects of the invention in view, there is also provided an electronic module which comprises:
 a first substrate including at least one first electrical contacting surface; and
 an electronic component including at least one second electrical contacting surface,
wherein the electronic component and the first substrate are joined to one another by way of a joint, and the joint encompasses the at least one first electrical contacting surface and the at least one second electrical contacting surface, and wherein the joint is surrounded or enclosed by a first material layer made of a thermoplastic material, which is joined to the electronic component and the first substrate.

According to a preferred embodiment of the electronic module according to the invention, it is provided that the first substrate is formed of a first thermoplastic polymer, preferably a first liquid crystal polymer, and the first material layer is formed of a second thermoplastic polymer, preferably a second liquid crystal polymer, wherein the first thermoplastic polymer has a higher glass transition temperature or melting temperature than the second thermoplastic material.

According to a further embodiment of the electronic module according to the invention, it is provided that the first substrate includes one or more recesses, in which one or more protrusions of the first material layer engage in a form-locking or form-fitting manner.

According to the preferred embodiment of the electronic module according to the invention, it is provided that the first substrate and/or the first material layer include a liquid crystal polymer or consist thereof.

According to a further embodiment of the electronic module according to the invention, it is provided that the electronic component is covered or enclosed by a second material layer made of a thermoplastic material. In one embodiment, the second material layer is constructed as a cover film or as a second substrate. In one embodiment, the second material layer includes a liquid crystal polymer or consists thereof.

According to a further embodiment of the electronic module according to the invention, it is provided that the joint includes at least one bump and/or a solder ball (solder bump). In one embodiment, the bump includes gold (gold stud bump), gold-coated copper (copper pillar bump), tinned gold, or tinned copper, or consists thereof. In one embodiment, the solder ball (solder bump) includes tin solder (for example Sn99, Ag0.3, Cu0.7 or another mixture of Sn, Ag and Cu, or, for example, Au80Sn20).

In particular, a desired distance between the electronic component and the first substrate may be adjusted by way of the height of the at least one bump or solder ball.

According to a further embodiment of the method according to the invention, it is provided that the at least one first contacting surface is constructed as a pad, wherein the pad is preferably substantially made of copper. In one embodiment, the at least one second contacting surface is constructed as a pad, wherein the pad is preferably substantially made of gold.

According to a further embodiment of the electronic module according to the invention, it is provided that the electronic component is constructed as an integrated semiconductor component, in particular an application-specific integrated circuit (ASIC), a standard integrated circuit (standard IC) or a wafer-level chip scale package (WL-CSP).

With the objects of the invention in view, there is furthermore provided a medical device, particularly an implantable medical device or a medical device that can be introduced into the body. The medical device comprises the electronic module according to the invention.

According to one embodiment, the medical device according to the invention is constructed as an implantable cardiac pacemaker, a cardioverter defibrillator, a neurostimulator, a diagnostic device (cardiac monitor) or a catheter.

Other features which are considered as characteristic for the invention are set forth in the appended claims.

Although the invention is illustrated and described herein as embodied in a method for producing an electronic module, an electronic module and a medical device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Examples

The present invention relates in particular to a thermocompression bonding method for joining electronic components 1, with an encapsulation of the joints in thermoplastic materials 3.

As a result of the method according to the invention, it is advantageously possible to create an electrical connection between electronic, active and passive components 1 and substrates 7 using a bonding process, while creating an encapsulation 3 as tight as possible using organic materials.

Advantageously, the method according to the invention can in particular be used during the production of implants without metal housings and catheters.

The approach according to the invention is superior to the related art in terms of cost and tightness, while achieving equivalent miniaturization, and allows corresponding miniaturized implants and catheters to be produced considerably more cost-effectively.

Figure 1A:
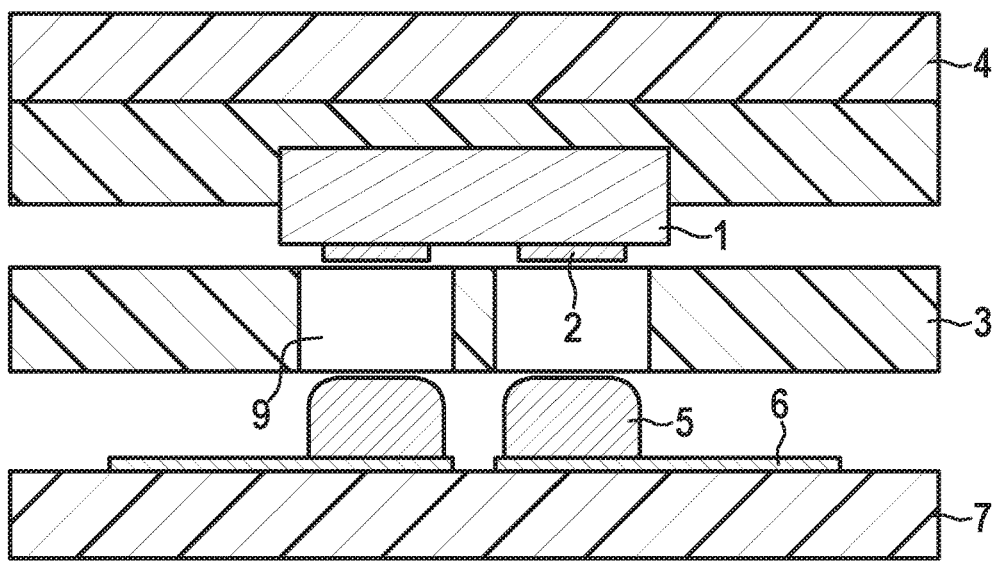
FIG. 1A is a diagrammatic, cross-sectional view through components to be joined prior to being compressed.
Figure 1B:
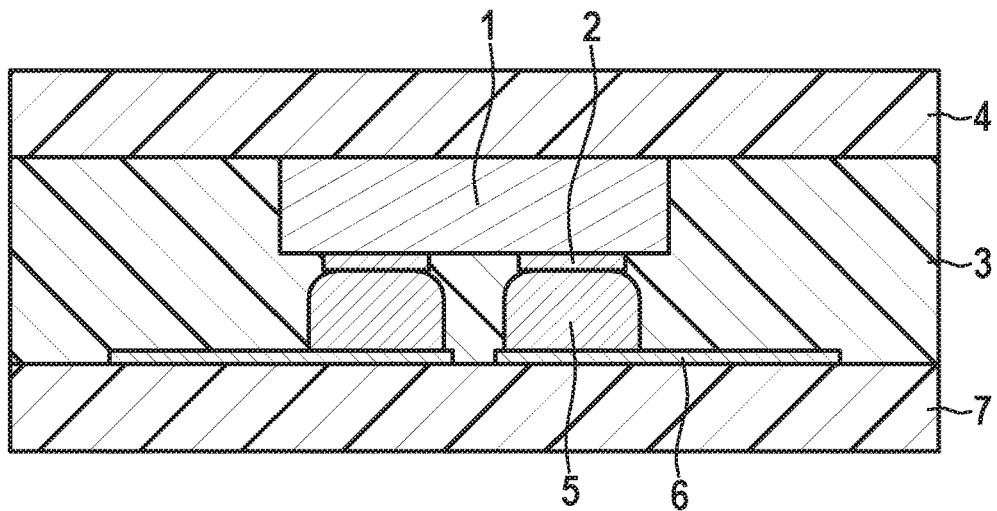
FIG. 1B is a cross-sectional view through the structure after compression.

Referring now to the figures of the drawings in detail and first, particularly, to FIGS. 1A and 1B thereof, the general concept according to the invention will be briefly described hereafter. A pattern 3 made of a thermoplastic material (preferably LCP) that is cut out at the positions 9 of the gold bumps 5 is placed on a substrate 7 including contact pads 6, and gold bumps 5 placed thereon (FIG. 1A). An electronic component 1 including contact pads 2 made of gold is placed thereabove with precise fit. Then, a cover material 4 follows. The entire stack is bonded or welded together using uniaxial pressure and heat. After the compression, the structure illustrated in FIG. 1B is obtained.

So as to achieve precisely fitting registration or alignment of the thermoplastic pattern 3 with respect to the substrate 7 and the electronic component 1, holes may be introduced into the pattern 3, the substrate 7 and the cover film 4 in such a way that all three layers 3, 4, 7 can be precisely aligned with one another using a pin.

Figure 2A:
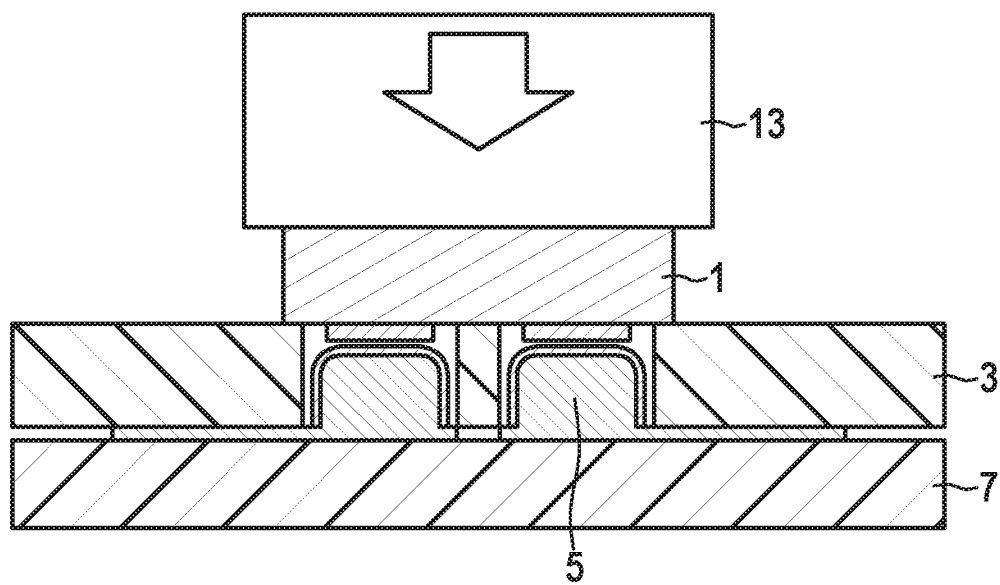
FIG. 2A is a cross-sectional view through components to be joined during the placement using a thermocompression bonder.

It is also possible to omit the cover film 4. The electronic component 1 is then placed onto the pattern 3 that is aligned with the substrate 7 using a so-called thermocompression bonder 13 (machines available on the market). The registration may take place by way of a camera on alignment marks on the substrate 7 or the pattern 3. As soon as the component 1 has been placed on the pattern 3, pressure is exerted via a holding tool 13 of the thermocompression bonder, and the temperature is raised to above the melting point of the thermoplastic pattern 3 (FIG. 2A).

Figure 2B:
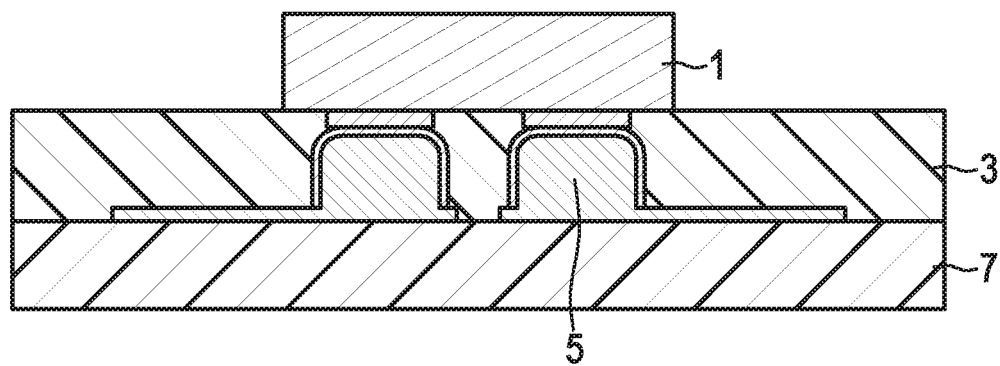
FIG. 2B is a cross-sectional view through the structure after the thermocompression bonding, wherein the components (the substrate and the electrical component) are pressed into the thermoplastic pattern, and the material of the pattern spreads between the bumps.

The holding tool 13 of the thermocompression bonder holds the electronic component 1 (for example by channels present in the tool 13, which can be evacuated), and allows the electronic component 1 to be precisely positioned on the thermoplastic pattern 3 and the substrate 7 via suitable optical registration marks in the thermoplastic pattern 3 or the substrate 7. Advantageously, conventional available thermocompression bonders may be used. The tool 13 is preferably constructed to apply a pressure of approximately several bars and a temperature profile of up to 350° C. for several minutes. The resulting structure is shown in FIG. 2B.

The material of the thermoplastic pattern 3 is a thermoplastic polymer, which is softened as a result of the temperature of the tool 13 so as to completely fill the spaces between the bumps 5 and the electronic component 1. The material of the pattern 3 is advantageously the same material as that of the substrate 7. When liquid crystal polymer (LCP) is the selected material, it is possible to use the same material at a higher melting point for the substrate 7, and at a lower melting point for the thermoplastic pattern 3. The temperature and pressure are selected in such a way that, on the one hand, the melting point or glass transition point of the pattern 3 is exceeded, but, on the other hand, also a reliable connection (intermetallic phase) is achieved between the gold contact of the bumps 5 on the substrate 7 and the bumps 5 or chip pads 2 on the electronic component 1. An intermetallic phase between gold layers already forms at pressures of approximately 30 bar and temperatures above 260° C.

Figure 3A:
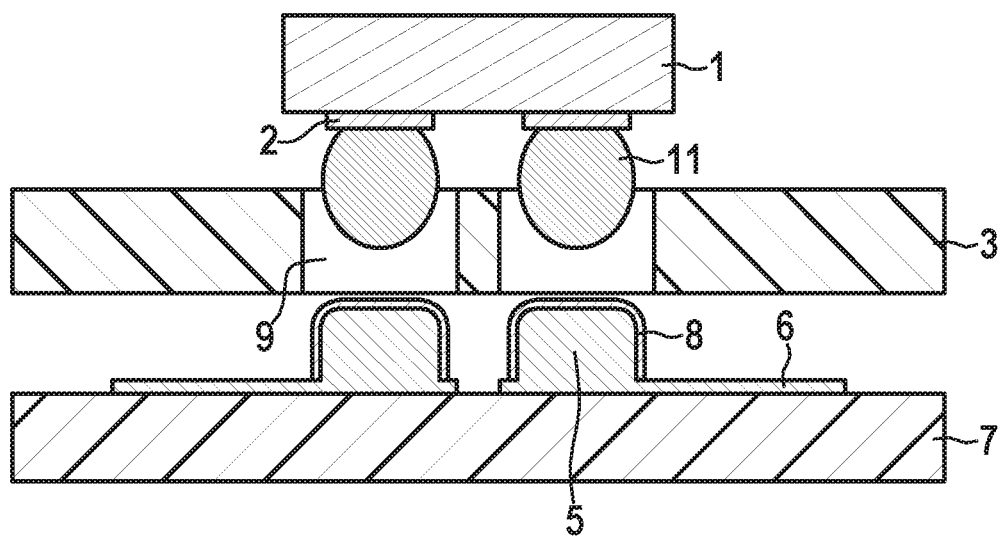
FIG. 3A is a cross-sectional view through components to be joined prior to the thermocompression bonding, wherein a component (electronic component) includes solder bumps, which are disposed on the contact surfaces of the electronic component.

The electronic component 1 is preferably an integrated semiconductor component (such as an ASIC or also a standard IC). The metallization of the IC pads 2 is preferably configured with gold stud bumps or copper pillar bumps, and, as an alternative, solder bumps 11 are also possible. The electronic component 1 can also be a wafer-level chip scale package (WL-CSP). The bumps 5 can also be made of copper including a coating made of gold 8 (FIG. 3A). The height of the bumps 5 is set in such a way that the desired distance between the electronic component 1 and the substrate 7 arises during bonding. The thickness of the pattern 3 is likewise suitably selected. These dimensions will depend on the dimensions of the pads 2 on the electronic component 1.

Figure 3B:
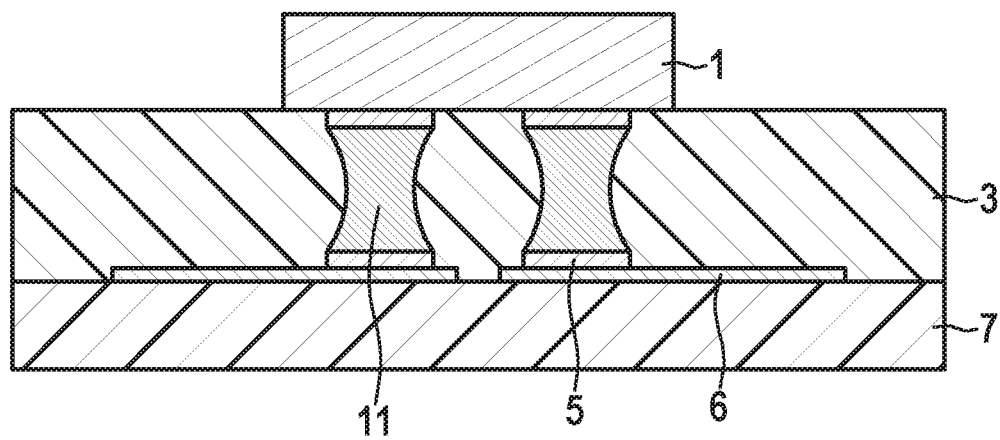
FIG. 3B is a cross-sectional view through the structure after the bonding of the electronic component with solder bumps, wherein the electronic component is pressed into the pattern, the material of the pattern spreads between the bumps, and the solder bumps are soldered to the pads on the substrate.
Figure 4A:
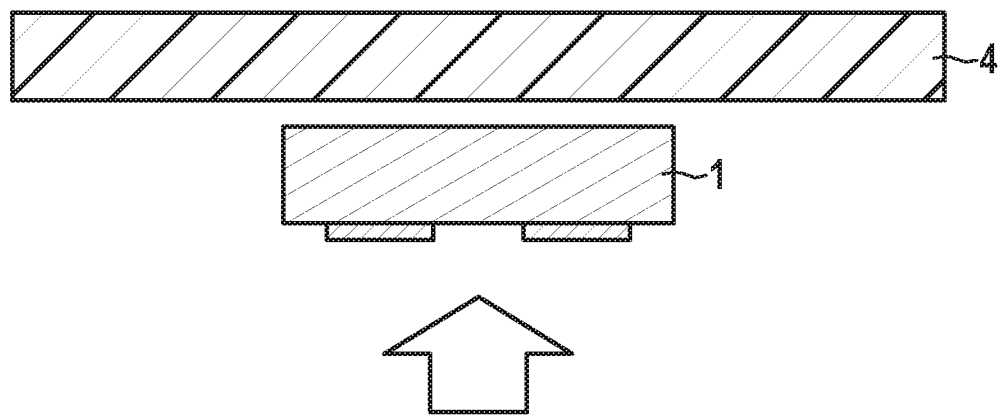
FIG. 4A is a cross-sectional view which shows the attachment of an electronic component onto a substrate.
Figure 4B:
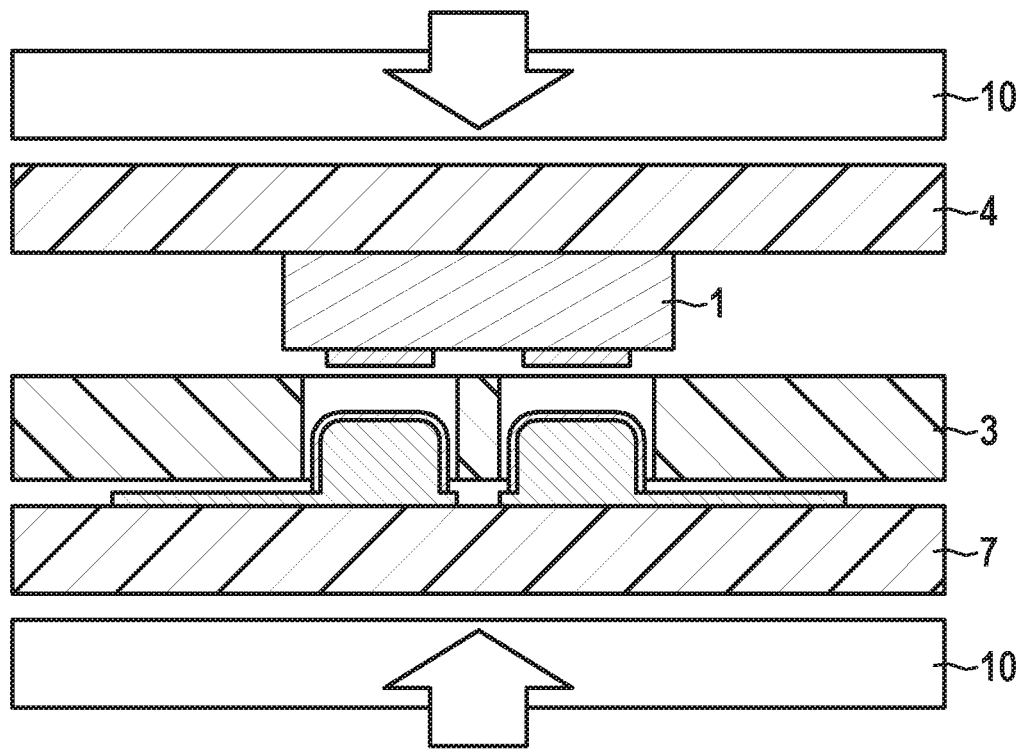
FIG. 4B is a cross-sectional view through the components to be joined prior to the compression using pressure and heat.
Figure 4C:
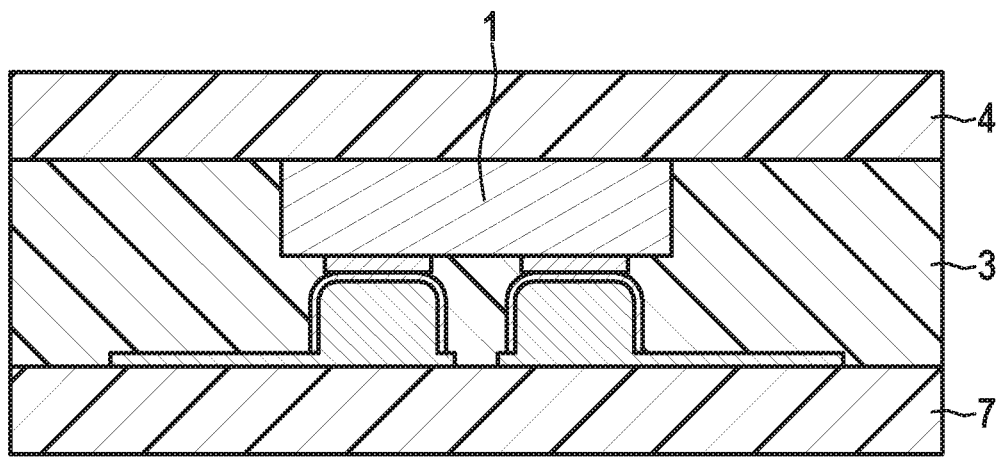
FIG. 4C is a cross-sectional view through the structure after the compression using pressure and heat, wherein the electrical component is completely embedded into the substrate.

When the electronic component 1 includes solder bumps 11, as is illustrated in FIG. 3A, the temperature has to be set by the tool 13 during bonding in such a way that both the pattern 3 flows, and the solder bumps are soldered to the bumps 5 on the substrate 7. When the solder bumps 11 are sufficiently large, the height of the bumps 5 can be reduced to the height of the conductor tracks 6, and only a thin gold layer 8 may be provided. Accordingly joined components are illustrated in FIG. 3B.

In a further embodiment, the electronic component 1 is first pushed onto a further substrate 4, using heat and pressure, and connected to the further substrate 4. As an alternative, the electronic component 1 can also be connected to the further substrate 4 using a suitable adhesive. The further substrate 4 is preferably made of a thermoplastic material, such as liquid crystal polymer (LCP).

Thereafter, the electronic component 1 thus prepared is positioned on the substrate 7 and the thermoplastic pattern 3. The positioning can also be carried out by suitable mechanical or optical registration. The entire package is placed between two heating plates 10. The stack is compressed by way of these heating plates 10 using a suitable pressure and temperature profile, the progression of which is selected in such a way that both the pads 2 of the electronic component 1 are electrically connected to the bumps 5 on the substrate 7, and the thermoplastic material of the pattern 3 flows between the bumps 5 and joins the entire package. The upper heating plate 10 can also be the tool of a thermocompression bonder 13.

In contrast to the preceding exemplary embodiments, the electronic component is completely embedded into the material of the substrates 7, 4 and the pattern 3 here. In this way, a multi-layer substrate, composed of the substrate layers 7 and 4, can be created.

Different chip pad metallurgies or solder bumps can also be used in this embodiment, wherein only the process parameters for the compression are adapted to the corresponding materials.

Figure 5A:
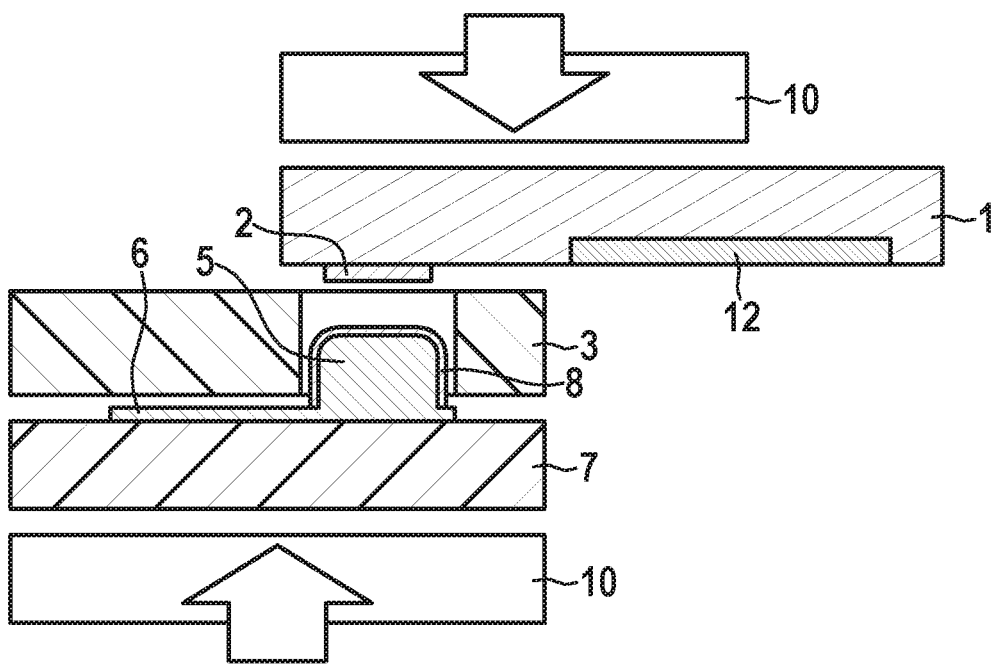
FIG. 5A is a cross-sectional view through the stack of a MEMS component including a membrane over a cavity prior to the compression using the heating plates or tools of a thermocompression bonder by using pressure and heat.
Figure 5B:
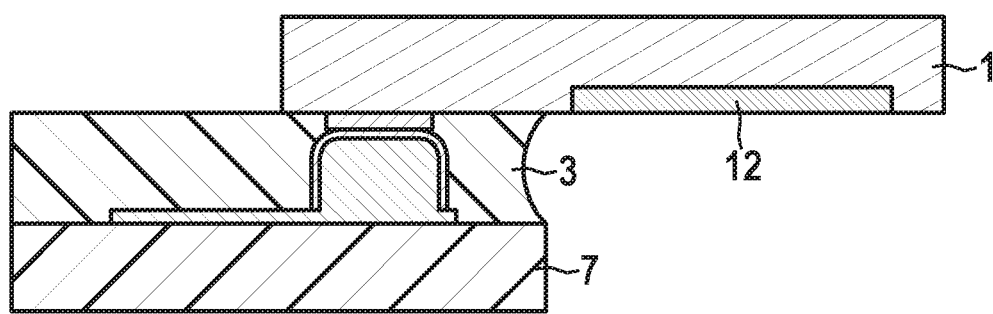
FIG. 5B is a cross-sectional view through the structure made of the MEMS component and the substrate after the compression, wherein a portion of the material of the pattern flows out on the open side.

The method according to the invention can likewise be applied to a MEMS component (micromechanical component), serving as the electronic component 1 to be joined, for example including a cavity that is closed by a membrane 12, wherein the membrane 12 is to remain open to the surrounding area. For this purpose, the thermoplastic pattern 3 and the substrates 7 and 4 preferably include corresponding openings, so that the membrane 12 is not covered. In this case, the tool 13 of the thermocompression bonder or the heating plates 10 is/are constructed in such a way that the thermoplastic pattern 3 is only heated in the region of the bumps 5 for the electrical connection, but not in the region of the membrane 12. After the compression, the structure illustrated in FIG. 5b is obtained.

The invention claimed is:

1. A method for producing an electronic module, the method comprising:
   providing a first substrate including at least one first electrical contacting surface, an electronic component including at least one second electrical contacting surface, and a first material layer made of a thermoplastic material having at least one recess extending through the first material layer;
   arranging the first substrate, the electronic component and the first material layer to place the first material layer between the first substrate and the electronic component, and to align the at least one first electrical contacting surface, the at least one second electrical contacting surface and the at least one recess relative to one another;

placing a second material layer, cover film, or second substrate made of a thermoplastic material on the electronic component;

thermocompression bonding the first substrate, the electronic component, the first material layer, and the second material layer to form a joint between the at least one first electrical contacting surface and the at least one second electrical contacting surface, and to surround or enclose the joint with the first material layer; and forming the first substrate of a first thermoplastic polymer, forming the first material layer of a second thermoplastic polymer, and providing the first thermoplastic polymer with at least one of a higher glass transition temperature or a higher melting temperature than the second thermoplastic material.

2. The method for producing an electronic module according to claim 1, wherein at least one of the first substrate or the first material layer consists of or includes a liquid crystal polymer.

3. The method for producing an electronic module according to claim 1, which further comprises providing the first substrate with one or more recesses, and causing the second thermoplastic polymer of the first material layer to flow in the one or more recesses during the thermocompression bonding.

4. The method for producing an electronic module according to claim 1, which further comprises providing the at least one first contacting surface or the at least one second contacting surface with a bump or solder ball.

5. The method for producing an electronic module according to claim 4, wherein the bump or solder ball includes or consists of gold, gold-coated copper, tinned gold or tinned copper.

6. The method for producing an electronic module according to claim 1, which further comprises carrying out the joining of the second material layer to the electronic component by thermocompression bonding or adhesive bonding, before, during or after the thermocompression bonding.

7. The method for producing an electronic module according to claim 1, which further comprises using the first substrate as a circuit board or a printed circuit board.

8. The method for producing an electronic module according to claim 1, which further comprises providing the electronic component as an integrated semiconductor component.

9. The method for producing an electronic module according to claim 1, which further comprises providing the integrated semiconductor component as an application-specific integrated circuit, a standard integrated circuit or a wafer-level chip scale package.

10. The method for producing an electronic module according to claim 1, which further comprises carrying out the thermocompression bonding at a temperature above the glass transition temperature.

11. The method for producing an electronic module according to claim 1, which further comprises carrying out the thermocompression bonding at a temperature above the melting temperature of the thermoplastic material.

12. The method for producing an electronic module according to claim 1, which further comprises carrying out the thermocompression bonding at a temperature above the melting temperature of the thermoplastic material of the first material layer, of the thermoplastic material of the first substrate or the thermoplastic material of the second material layer.

13. An electronic module, comprising:
a first substrate including at least one first electrical contacting surface, said first substrate being formed of a first thermoplastic polymer;
an electronic component including at least one second electrical contacting surface;
a joint joining said electronic component and said first substrate to one another, said joint including said at least one first electrical contacting surface and said at least one second electrical contacting surface;
a first material layer surrounding or enclosing said joint, said first material layer being made of a second thermoplastic polymer, said first material layer being joined to said electronic component and to said first substrate; and
a second material layer, cover film or second substrate made of a thermoplastic material covering or enclosing said electronic component,
wherein said first thermoplastic polymer has at least one of a higher glass transition temperature or a higher melting temperature than said second thermoplastic polymer.

14. The electronic module according to claim 13, wherein at least one of said first substrate or said first material layer includes a liquid crystal polymer or consist of a liquid crystal polymer.

15. The electronic module according to claim 13, wherein said first substrate has one or more recesses, and said first material layer has one or more protuberances each engaging form-lockingly in a respective one of said one or more recesses.

16. The electronic module according to claim 13, wherein said second material layer includes a liquid crystal polymer or consists of a liquid crystal polymer.

17. The electronic module according to claim 13, wherein said joint includes at least one of a bump or a solder ball.

18. The electronic module according to claim 17, wherein said bump or solder ball includes or consists of gold, gold-coated copper, tinned gold or tinned copper.

19. A medical device or implantable medical device, comprising an electronic module according to claim 13.

* * * * *